(12) United States Patent
Dos Santos et al.

(10) Patent No.: US 8,343,507 B2
(45) Date of Patent: Jan. 1, 2013

(54) **PROTEIN FROM *PHOTOBACTERIUM DAMSELAE* AND USE THEREOF**

(75) Inventors: Nuno Miguel Simoes Dos Santos, Torreira (PT); Ana Maria Silva Do Vale, Lavra (PT); Manuel Alexandre Teixera Da Silva, Porto (PT); Jorge Eduardo Da Silva Azevedo, Gaia (PT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/493,909

(22) Filed: Jun. 11, 2012

(65) Prior Publication Data

US 2012/0264172 A1 Oct. 18, 2012

Related U.S. Application Data

(62) Division of application No. 10/563,276, filed as application No. PCT/EP2004/008464 on Jul. 28, 2004, now Pat. No. 8,197,827.

(30) Foreign Application Priority Data

Jul. 29, 2003 (GB) .................................. 0317733.4

(51) Int. Cl.
*A61K 39/02* (2006.01)
*G01N 33/554* (2006.01)
*G01N 33/569* (2006.01)
*C12P 21/06* (2006.01)
*C07K 1/00* (2006.01)
*C07K 14/00* (2006.01)
*C07K 17/00* (2006.01)

(52) U.S. Cl. .................. 424/234.1; 435/7.32; 435/69.1; 530/350

(58) Field of Classification Search .......................... None
See application file for complete search history.

(56) References Cited

U.S. PATENT DOCUMENTS 5,587,166 A * 12/1996 Donachie .................. 424/255.1
6,087,336 A 7/2000 Edwards et al.
8,197,827 B2 6/2012 Dos Santos et al.

FOREIGN PATENT DOCUMENTS

EP 0773295 5/1997
JP 05-139994 * 6/1993
WO WO 96/12734 5/1996
WO WO 01/10459 2/2000

OTHER PUBLICATIONS

JP 05-139994. Jun. 1993. machine translation to English. Translated Aug. 25, 2012. 23 pages.*
Magarinos et al, "Vaccination Trials on Gilthead Seabream (*Sparus aurata*) against Pasteurella Piscidida", Aquaculture, vol. 120, No. 3-4, pp. 201-208, (1994).
Bakopoulos et al, "Vaccination Trials of Sea Bass *Dicentrarchus labrax* (L.), against *Photobacterium damsela* Subsp. piscicida using Novel Vaccine Mixtures", Journal of Fish Diseases, vol. 26, No. 2, pp. 77-90, (2003).
Magarinos et al, "Influence of Fish Size and Vaccine Formulation on the Protection of Gilthead Seabream Against *Pasteurella piscicida*", Bulletin of the European Association of Fish Pathologists, vol. 14, No. 4, pp. 120-122, (1994).
Mazzolini et al, "Pathogenic Variability of *Pasteurella piscicida* During in Vitro Cultivation as a Preliminary Study for Vaccine Production", Journal of Applied Ichthyology, vol. 14, No. 3/4, pp. 265-268, (1998).
Romalde et al, "Immunization with Bacterial Antigens: Pasteurellosis", Developments in Biological Standardization; Fish Vaccinology, pp. 167-177, (1997).
Magarinos et al, "Pathogenic Activities of Live Cells and Extracellular Products of the Fish Pathogen *Pasteurella piscicida*", Journal of General Microbiology, vol. 138, No. part 12, pp. 2491-1287 (1992).

* cited by examiner

*Primary Examiner* — Marcela M Cordero Garcia

(57) ABSTRACT

A derivative of a 55 kDa extracellular protein from *Photobacterium damselae* subsp. *piscicida* is the basis for a vaccine against *Photobacterium* infection, and thereby protects fish from pasteurellosis.

18 Claims, 2 Drawing Sheets

Figure 1: Nucleic acid sequence of p55 (SEQ ID NO:1)

```
ATGACAGCAATATTTTCTCTAGCCATAAACTCAAATTTTGTGTTAGCGAACAACGATAA
ACCAGATGCAAGCGATGACAAGTACGCAGACTACGTGGTACGTCTAGGTTCGGAACATC
CACTAAACCATACTCAGATCATTGAACTTTCCTCTGCAGTATCGAGGGCTGTCCTTCTT
AGTTACCCAAATATAATAGACCGATACACCGCTGCAGCAACTGAATATACGGTGATCGA
TGCTTTATTTCATTCGCCTACCTTTCGACATATCGTTTCTTTTGGTCTTCATAATCAGC
AAGAGAACCTTGGTCATATTCGATATACTAATGAATATGAAATTAACAATAATCGCGAA
GATGAGTTCTCCTTAGTGAGCGAGGTAAGCTACGACGATATAAAAGCTCTAATGCTCA
GCAAGTTCCCCTAGTTGCATTTTATGAAGCGCGAGAGGACCGCGCGACGGGCACGCCTA
TCGTAAATATGGGTGTAGCTCCTAGTCTTTTTTCTGGCAGATATAGTTGGTGGCAAGAA
GCATTAATCCATGAAATTGTTCATCACGTTACAGGCTCTAGTGATACTCATGAAGAAAA
TAAGCAAGGGCCTACTGAAATTTTAGCTCAAATGGTCGCGGCGGAACTTCATTGGGCGA
TACCAACCTTTAAAGGATATTCAGATCCTGCGAGGGTCGAAGCGATACAAGAGCGCGAT
TTCCACTCCTTGTTGAATATGTTCCAGAGACACGGCAGTGAATTAGGCTTTCTGTTCAC
CAGATTAGCTACGATTGCCAAAGGTAAGAAAGCTTCGCCTGACTTCGGCACCCTGACCT
CTTTTTGCTCGGAAGGTATTAGCAGTTTTCCTAAATATCCCGATCACGATGATGATTTC
AACGGGGGCGGCGCCTTTTTTCTCCCTAGCGCTAGCGCCGACAGTTCAGTTGAATGCAC
TTTTGATGTACTAAATCGAATCGAGCCTGTTGATGACTCAATTAAATTTGAAGGGGGA
ATTTGCTAATTAAAAATGACTTCAAAAACCTAAATTTACGTGTTGCACAGCTTAGCTTT
TTGAACGCAAAAAAAGGTAGCGGATTTTACAGAAAAAATTGGGATTCTTGGAAATCCTG
GTATCAAGCTTCTTCATGGAAGAATGGGCTCAATTCCGGTCTATATGGGTACGGCCATG
ATGAATCTGAAGGAAACCTCATTTATTCTCCATATGGCATAACCTTCAATGATGGTTCA
TTCTCTATTGGCTTTTCATCGAGAAAGCATATTAATGACAACACGAAGGATGACAATTT
CGTGAAGTTAAATAACGCTAATTGGAGTTCGTTCTACTACGCAGGTCAAATGTTTTTTG
ACAAAAACAAAAGACCTGTAGCGCTTGTTATTACGGAGCCTTTAAATGCTGCTTTTGGC
GCAGGATGGTCTTATATTTATAAAGATGGGAAATGGCACTATGAAGCTCAAGACGATTG
GGATCAGCGTCTATTTAAAGATTCGACCTTGTCGTTGGATCCCCACGCGCCACAATTCA
TTAATTAA
```

Figure 2: Amino acid sequence of p55 (SEQ ID NO:2)

```
MTAIFSLAINSNFVLANNDKPDASDDKYADYVVRLGSEHPLNHTQIIELSSAVSRAVLLSYPN
IIDRYTAAATEYTVIDALFHSPTFRHIVSFGLHNQQENLGHIRYTNEYEINNNREDEFSLVSE
VSYDDIKSSNAQQVPLVAFYEAREDRATGTPIVNMGVAPSLFSGRYSWWQEALIHEIVHHVTG
SSDTHEENKQGPTEILAQMVAAELHWAIPTFKGYSDPARVEAIQERDFHSLLNMFQRHGSELG
FLFTRLATIAKGKKASPDFGTLTSFCSEGISSFPKYPDHDDDFNGGGAFFLPSASADSSVECT
FDVLNRIEPVDDSIKFEGGNLLIKNDFKNLNLRVAQLSFLNAKKGSGFYRKNWDSWKSWYQAS
SWKNGLNSGLYGYGHDESEGNLIYSPYGITFNDGSFSIGFSSRKHINDNTKDDNFVKLNNANW
SSFYYAGQMFFDKNKRPVALVITEPLNAAFGAGWSYIYKDGKWHYEAQDDWDQRLFKDSTLSL
DPHAPQFIN-
```

SEQUENCE LISTING

```
<160> NUMBER OF SEQ ID NOS: 6

<210> SEQ ID NO 1
<211> LENGTH: 1542
<212> TYPE: DNA
<213> ORGANISM: Photobacterium damselae
<400> SEQUENCE: 1
atgacagcaa tatttctct agccataaac tcaaatttg tgttagcgaa caacgataaa      60
ccagatgcaa gcgatgacaa gtacgcagac tacgtggtac gtctaggttc ggaacatcca     120
ctaaaccata ctcagatcat tgaactttcc tctgcagtat cgagggctgt ccttcttagt     180
tacccaaata taatagaccg atacaccgct gcagcaactg aatatacggt gatcgatgct     240
ttatttcatt cgcctacctt tcgacatatc gtttcttttg gtcttcataa tcagcaagag     300
aaccttggtc atattcgata tactaatgaa tatgaaatta acaataatcg cgaagatgag     360
ttctccttag tgagcgaggt aagctacgac gatataaaaa gctctaatgc tcagcaagtt     420
cccctagttg cattttatga agcgcgagag gaccgcgcga cggcacgcc tatcgtaaat     480 atgggtgtag ctcctagtct tttttctggc agatatagtt ggtggcaaga agcattaatc     540
catgaaattg ttcatcacgt tacaggctct agtgatactc atgaagaaaa taagcaaggg     600
cctactgaaa ttttagctca aatggtcgcg gcggaacttc attgggcgat accaaccttt     660
aaaggatatt cagatcctgc gagggtcgaa gcgatacaag agcgcgattt ccactccttg     720
ttgaatatgt tccagagaca cggcagtgaa ttaggctttc tgttcaccag attagctacg     780
attgccaaag gtaagaaagc ttcgcctgac ttcggcaccc tgacctcttt ttgctcggaa     840
ggtattagca gttttcctaa atatcccgat cacgatgatg atttcaacgg gggcggcgcc     900
ttttttctcc ctagcgctag cgccgacagt tcagttgaat gcacttttga tgtactaaat     960
cgaatcgagc ctgttgatga ctcaattaaa tttgaagggg ggaatttgct aattaaaaat    1020
gacttcaaaa acctaaattt acgtgttgca cagcttagct ttttgaacgc aaaaaaaggt    1080
```

```
agcggatttt tacagaaaaaa ttgggattct tggaaatcct ggtatcaagc ttcttcatgg    1140
aagaatgggc tcaattccgg tctatatggg tacggccatg atgaatctga aggaaacctc    1200
atttattctc catatggcat aaccttcaat gatggttcat tctctattgg cttttcatcg    1260
agaaagcata ttaatgacaa cacgaaggat gacaatttcg tgaagttaaa taacgctaat    1320
tggagttcgt tctactacgc aggtcaaatg ttttttgaca aaacaaaag acctgtagcg     1380 cttgttatta cggagccttt aaatgctgct tttggcgcag atggtctta tatttataaa     1440 gatgggaaat ggcactatga agctcaagac gattgggatc agcgtctatt taaagattcg    1500
accttgtcgt tggatcccca cgcgccacaa ttcattaatt aa                       1542
```

<210> SEQ ID NO 2
<211> LENGTH: 513
<212> TYPE: PRT
<213> ORGANISM: Photobacterium damsela

<400> SEQUENCE: 2

```
Met Thr Ala Ile Phe Ser Leu Ala Ile Asn Ser Asn Phe Val Leu Ala
1               5                   10                  15

Asn Asn Asp Lys Pro Asp Ala Ser Asp Lys Tyr Ala Asp Tyr Val
            20                  25                  30

Val Arg Leu Gly Ser Glu His Pro Leu Asn His Thr Gln Ile Ile Glu
        35                  40                  45

Leu Ser Ser Ala Val Ser Arg Ala Val Leu Leu Ser Tyr Pro Asn Ile
    50                  55                  60

Ile Asp Arg Tyr Thr Ala Ala Thr Glu Tyr Thr Val Ile Asp Ala
65                  70                  75                  80

Leu Phe His Ser Pro Thr Phe Arg His Ile Val Ser Phe Gly Leu His
                85                  90                  95

Asn Gln Gln Glu Asn Leu Gly His Ile Arg Tyr Thr Asn Glu Tyr Glu
            100                 105                 110

Ile Asn Asn Asn Arg Glu Asp Glu Phe Ser Leu Val Ser Glu Val Ser
        115                 120                 125

Tyr Asp Asp Ile Lys Ser Ser Asn Ala Gln Gln Val Pro Leu Val Ala
    130                 135                 140

Phe Tyr Glu Ala Arg Glu Asp Arg Ala Thr Gly Thr Pro Ile Val Asn
145                 150                 155                 160

Met Gly Val Ala Pro Ser Leu Phe Ser Gly Arg Tyr Ser Trp Trp Gln
                165                 170                 175

Glu Ala Leu Ile His Glu Ile Val His Val Thr Gly Ser Ser Asp
            180                 185                 190

Thr His Glu Glu Asn Lys Gln Gly Pro Thr Glu Ile Leu Ala Gln Met
    195                 200                 205

Val Ala Ala Glu Leu His Trp Ala Ile Pro Thr Phe Lys Gly Tyr Ser
    210                 215                 220

Asp Pro Ala Arg Val Glu Ala Ile Gln Glu Arg Asp Phe His Ser Leu
225                 230                 235                 240

Leu Asn Met Phe Gln Arg His Gly Ser Glu Leu Gly Phe Leu Phe Thr
                245                 250                 255

Arg Leu Ala Thr Ile Ala Lys Gly Lys Lys Ala Ser Pro Asp Phe Gly
            260                 265                 270

Thr Leu Thr Ser Phe Cys Ser Glu Gly Ile Ser Ser Phe Pro Lys Tyr
    275                 280                 285

Pro Asp His Asp Asp Asp Phe Asn Gly Gly Gly Ala Phe Phe Leu Pro
```

```
            290                 295                 300
Ser Ala Ser Ala Asp Ser Ser Val Glu Cys Thr Phe Asp Val Leu Asn
305                 310                 315                 320

Arg Ile Glu Pro Val Asp Asp Ser Ile Lys Phe Glu Gly Gly Asn Leu
                325                 330                 335

Leu Ile Lys Asn Asp Phe Lys Asn Leu Asn Leu Arg Val Ala Gln Leu
            340                 345                 350

Ser Phe Leu Asn Ala Lys Lys Gly Ser Gly Phe Tyr Arg Lys Asn Trp
        355                 360                 365

Asp Ser Trp Lys Ser Trp Tyr Gln Ala Ser Ser Trp Lys Asn Gly Leu
    370                 375                 380

Asn Ser Gly Leu Tyr Gly Tyr Gly His Asp Glu Ser Glu Gly Asn Leu
385                 390                 395                 400

Ile Tyr Ser Pro Tyr Gly Ile Thr Phe Asn Asp Gly Ser Phe Ser Ile
                405                 410                 415

Gly Phe Ser Arg Lys His Ile Asn Asp Asn Thr Lys Asp Asp Asn
            420                 425                 430

Phe Val Lys Leu Asn Asn Ala Asn Trp Ser Ser Phe Tyr Tyr Ala Gly
        435                 440                 445

Gln Met Phe Phe Asp Lys Asn Lys Arg Pro Val Ala Leu Val Ile Thr
    450                 455                 460

Glu Pro Leu Asn Ala Ala Phe Gly Ala Gly Trp Ser Tyr Ile Tyr Lys
465                 470                 475                 480

Asp Gly Lys Trp His Tyr Glu Ala Gln Asp Asp Trp Asp Gln Arg Leu
                485                 490                 495

Phe Lys Asp Ser Thr Leu Ser Leu Asp Pro His Ala Pro Gln Phe Ile
            500                 505                 510

Asn

<210> SEQ ID NO 3
<211> LENGTH: 18
<212> TYPE: PRT
<213> ORGANISM: Photobacterium damsela

<400> SEQUENCE: 3

Asn Asn Asp Lys Pro Asp Ala Ser Asp Asp Lys Tyr Ala Asp Tyr Val
1               5                   10                  15

Val Arg

<210> SEQ ID NO 4
<211> LENGTH: 21
<212> TYPE: PRT
<213> ORGANISM: Photobacterium damsela

<400> SEQUENCE: 4

Tyr Thr Ala Ala Ala Thr Glu Tyr Thr Val Ile Asp Ala Leu Phe His
1               5                   10                  15

Ser Pro Thr Phe Arg
            20

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
```

-continued

```
ggccatgatg aatctgaagg                                                 20

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
gtaatacgac tcactatagg gc                                              22
```

US 8,343,507 B2

PROTEIN FROM *PHOTOBACTERIUM DAMSELAE* AND USE THEREOF

CROSS-REFERENCE TO RELATED APPLICATIONS

This application claims priority to U.S. application Ser. No. 10/563,276, now U.S. Pat. No. 8,197,827, filed Jan. 4, 2006, which claims priority to PCT Application Number PCT/EP2004/08464, filed Jul. 28, 2004, which claims priority to GB Application Number 0317733.4, filed Jul. 29, 2003.

FIELD OF THE INVENTION

The invention relates to a novel secreted protein from *Photobacterium damselae* subsp. *piscicida*, and to use of the protein or a nucleic acid sequence encoding the protein in a vaccine against pasteurellosis in fish.

BACKGROUND OF THE INVENTION

Mortalities resulting from infections with *Photobacterium damselae* subsp. *piscicida* (formerly *Pasteurella piscicida*) cause the most significant losses in warm water marine aquaculture worldwide. The disease (pasteurellosis) has great economic impact in Japan, where it affects mainly yellowtail cultures, and in the Mediterranean area, due to the losses it causes in sea bream and sea bass farms. Antibiotic therapy is generally ineffective and undesirable due to its negative environmental impact. The development of a vaccine against this disease has been slow, predominantly as a result of the pathogen being facultatively intracellular, and therefore not generally exposed to immune defence mechanisms. Until now, vaccine research has focused on bacterins prepared from heat- or formalin-killed cells. A bacterin vaccine enriched in extracellular products (ECPs) called "D121" has been commercialized in certain European countries. The degree of efficacy obtained with these bacterins is highly variable and the duration of protection is often short.

There is an unmet need in the field to deliver an inexpensive, easy to manufacture, and reproducibly effective vaccine against *Photobacterium* infection.

SUMMARY OF THE INVENTION

In a first aspect, the invention provides an isolated or purified 55 kDa extracellular protein from *Photobacterium damselae* subsp. *piscicida*, or a derivative thereof, and antibodies raised thereto.

In a second aspect the invention provides an isolated nucleic acid sequence encoding the 55 kDa protein or a homologue or fragment thereof, or a sequence which hybridizes thereto under stringent conditions. Also provided are a DNA expression vector carrying the p55 nucleic acid sequence, and a host cell transformed with the DNA expression vector.

In a third aspect, the invention provides a vaccine composition comprising an isolated or purified 55 kDa extracellular protein from *Photobacterium damselae* subsp. *piscicida*, or a derivative thereof, and a pharmaceutically acceptable carrier.

In a further aspect, the invention provides the use of an isolated or purified 55 kDa extracellular protein from *Photobacterium damselae* subsp. *piscicida*, or a derivative thereof, as a medicament.

In another aspect, the invention provides the use of an isolated or purified 55 kDa extracellular protein from *Photobacterium damselae* subsp. *piscicida*, or a derivative thereof, in the manufacture of a medicament for the prevention or treatment of pasteurellosis in fish.

In yet another aspect, the invention provides a method of preventing or treating pasteurellosis in fish, comprising administering to a fish a vaccine composition comprising an isolated or purified 55 kDa extracellular protein from *Photobacterium damselae* subsp. *piscicida*, or a derivative thereof, and a pharmaceutically acceptable carrier.

In a further aspect, the invention provides a method of preparing a vaccine against pasteurellosis, comprising the steps:
(a) growing *Photobacterium damselae* subsp. *piscicida* cells in culture, optionally to mid-exponential phase;
(b) separating supernatant from the cells;
(c) optionally, concentrating the supernatant; and
(d) inactivating the supernatant with an inactivating agent.

The inactivating agent is preferably formaldehyde. Also comprised within the invention is a vaccine composition comprising an inactivated cell culture supernatant from *Ph. damselae* subsp. *piscicida*, wherein said cell culture supernatant is rich in p55.

DESCRIPTION OF THE FIGURES

FIG. 1 (SEQ ID NO:1) shows the DNA sequence of the p55 protein identified in MT1415 (a virulent strain of *Ph. damselae* subsp. *piscicida*).

FIG. 2 (SEQ ID NO:2) shows the deduced amino acid sequence of p55; the 16 amino acid signal sequence which may be cleaved to form the mature protein is shadowed.

DETAILED DESCRIPTION OF THE INVENTION

The protein which is the subject of the present invention was purified from a preparation of extracellular products (ECP) from virulent *Photobacterium damselae* susp. *piscicida*. By SDS-PAGE this purified protein was judged to run alongside a 55 kDa marker. For convenience, this protein shall be referred to as the 55 kDa protein or p55. It has been discovered that this protein plays an important role in inducing apoptosis in peritoneal phagocytes during infection. The 55 kDa protein has been cloned and sequenced; the DNA sequence and deduced amino acid sequence are depicted in FIGS. 1 and 2, respectively. The "isolated" p55 gene or nucleic acid sequence is understood to mean the gene or sequence other than in its natural context within the *Ph. damselae* genome.

The 55 kDa protein of the present invention is distinct from the so-called 55 kDa ECP protein complex from *Photobacterium* disclosed in WO 01/10459, which in fact is nearer to 52 kDa in size. That 55 kDa ECP complex was shown to consist of at least two different entities, neither of which has an N-terminal sequence related to the p55 sequence disclosed herein. The 55 kDa ECP complex of WO 01/10459 is expressed in iron supplemented culture conditions, whereas the 55 kDa protein of the present invention is the major secreted protein at mid-exponential phase independent of the level of iron in the culture medium. Furthermore, when antiserum raised against the WO 01/10459 55 kDa ECP complex was used to treat ECP preparations to remove this protein, the apoptogenic properties of the treated ECP preparation were unaffected.

We wished to assess whether immunization of fish with purified native p55 might provoke a protective immune response against *Photobacterium* infection. However, the protein was found to be highly toxic to fish when administered in native purified form, leading to rapid death. Instead, we used a method of passive administration to demonstrate that antibodies raised against this 55 kDa protein in rabbits (which specifically bind to the p55 secreted by virulent *Photobacterium* cells in vivo) are capable of reducing *Photobacterium*-related mortalities to a significant degree (Example 3).

The benefits of passive immunization can be surpassed by active immunization, whereby antibodies are raised to the 55 kDa protein by the fish themselves, following vaccination with a derivative of the protein which is less toxic than the native form, as demonstrated in Example 4.

A "derivative" of the protein refers to a variant of the 55 kDa protein which has an altered primary, secondary and/or tertiary amino acid sequence compared to the naturally-occurring (native) protein; it includes the native 55 kDa protein which has undergone one or more chemical or physical processing steps resulting in a reduction in toxicity of the protein to fish. The derivative may lack or may include the signal sequence (amino acids 1-16). An "immunogenic" derivative is one capable of eliciting antibodies that neutralize pathogen infectivity and/or mediate antibody-complement or antibody dependent cell cytotoxicity to provide protection against pasteurellosis in an immunized host. The immunogenicity of a derivative can be tested by immunizing an animal and checking to see whether antiserum from the animal is capable of specifically recognizing p55 (e.g. by Western blotting analysis). A detoxified immunogenic derivative of p55, when administered to susceptible fish, results in a positive RPS (relative percent survival) relative to saline-injected control fish when both are challenged with virulent *Ph. damselae*.

For instance, a detoxified immunogenic derivative of the 55 kDa protein may be a substantially homologous recombinant variant which has been engineered by site-directed mutagenesis to eliminate or reduce the toxicity of the protein to fish, yet maintain the ability to induce, in fish, the production of antibodies that recognize and (cross-)react with the antigens from *Photobacterium* and/or to induce an immune response in fish that protects against infection with this pathogen.

Alternatively, the derivative may be native p55 or isolated or purified p55 which has been subjected to heat treatment, microwaves, light, water treatment, sonication, cold treatment, freezing, freezing and thawing, lyophilization, denaturation with urea or detergents, formaldehyde treatment, or any other treatment known to cause alterations in the 3D conformation of proteins.

The derivative of native p55 may be provided in the form a preparation of extracellular products from *Ph. damselae* subsp. *piscicida*. We have discovered that p55 is the major secreted protein in bacterial cultures grown to mid-exponential phase, constituting greater than 85% of the secreted protein under these conditions (older bacterial supernatants—late exponential to stationary phase—have a much more complex protein pattern, although p55 is also present). The invention in one aspect relates in general to inactivated ECP preparations enriched in p55 for use in vaccines. Preferably these ECP preparations are prepared under normal iron conditions, i.e. the cells are grown in culture medium neither supplemented with iron nor incorporating iron chelating agents. The iron concentration of the medium is preferably <15 µM, more preferably <10 µM, more preferably <1 µM, and most preferably <0.1 µM. A preferred embodiment of the invention relates to a vaccine comprising a concentrated culture supernatant from *Ph. damselae* subsp. *piscicida*, preferably grown to mid-exponential phase, which has been inactivated. "Mid-exponential phase" means to an optical density (OD) at 600 nm of 0.5-0.7, preferably 0.55-0.65, more preferably about 0.6. The supernatant is preferably separated away from the cells before the inactivation step. The cell culture supernatant is optionally concentrated for use (before or after inactivation), for instance 1.5-200 fold, optionally 5-150 fold, for example 50-100 fold. Conventional methods for concentrating the supernatant can be employed, including centrifugal filter devices, ultracentrifugation, vacuum dialysis, ammonium sulphate precipitation, and the like. Example 1 indicates one way of preparing a concentrated culture supernatant, and Example 4 teaches an inactivation step with formaldehyde. Suitable examples of inactivating agents include formaldehyde, saponins, beta-propiolactone (BPL), and binary ethyleneimine (BEI).

In one embodiment the derivative is recombinantly expressed, having an identical amino acid sequence to the native p55 (plus/minus signal sequence), but as a consequence of recombinant expression within a host cell the folding, glycosylation or other post-translational processing of the protein differs from that of the protein in the native state. Any differences in conformation or chemical properties can be reflected in reduced toxicity to fish. For instance, the recombinantly expressed protein from *E. coli* used for immunization in Example 4 forms inclusion bodies, probably due to misfolding.

The derivative may be a non-toxic portion, fragment or epitope of the protein, for instance prepared by cloning and recombinant expression of the protein, or by enzymatic cleavage and/or chemical cleavage of the protein, followed by purification of a protein fragment. In one embodiment the derivative is a fragment of p55, prepared by digestion with a proteolytic enzyme such as trypsin or by cleavage with a chemical such as cyanogen bromide.

For present purposes a "portion" or "fragment" of the p55 protein is understood to mean any peptide molecule having at least 6, preferably at least 10, more preferably at least 15, more preferably at least 25, optionally at least 35, or at least 45 contiguous amino acids of the 55 kDa protein. A "portion" of the protein may be the full-length amino acid sequence.

An "isolated" or "purified" protein is defined as being substantially free of cellular material or other contaminating proteins from the cell or tissue source from which the protein is derived, or substantially free from chemical precursors or other chemicals when chemically synthesized. The language "substantially free of cellular material" includes preparations of the protein in which the protein is separated from cellular components of the cells from which it is isolated or recombinantly produced. In one embodiment, the language "substantially free of cellular material" includes preparations of 55 kDa protein having less than about 30% (by dry weight) of non-55 kDa protein (also referred to herein as a "contaminating protein"), more preferably less than about 20% of contaminating protein, still more preferably less than about 10% of contaminating protein, and most preferably less than about 5% contaminating protein. When the 55 kDa protein or biologically active portion thereof is recombinantly produced, it is also preferably substantially free of culture medium, i.e., culture medium represents less than about 20%, more preferably less than about 10%, and most preferably less than about 5% of the volume of the protein preparation.

There are several different geographical isolates of *Photobacterium damselae* susp. *piscicida*. Examples of strains familiar to researchers in the field include MT1415, PP3, MT1375, MT1588, MT1594, DI 21, B51, EPOY 8803-II, PTAVSA95, ATCC 29690, CECT (Colección Espanola de Cultivos Tipo) 4780, CECT 4781, CECT 5063 and CECT 5064. There is a certain degree of variation in nucleic acid sequence of these strains and in the amino acid sequences of the proteins they express. The 55 kDa protein used in the invention is not restricted to any specific strain source but it may be absent from certain non-virulent strains of *Ph. damselae*, such as ATCC 29690 and EPOY 8803-II. A skilled person can easily test for absence of this protein in a strain by SDS-PAGE analysis or Western blotting analysis, by PCR, or by replicating the apoptosis assay described in do Vale et al. Fish & Shellfish Immunology 15 (2003): 129-144. There may be an advantage in matching the 55 kDa variant with the prevalent strain in a particular geographical zone when designing a vaccine for that area.

The invention encompasses derivatives being nucleic acid sequences and amino acid sequences which are substantially homologous to the sequences provided in SEQ ID NO:1 and SEQ ID NO:2, respectively. "Substantially homologous" means that a sequence, when compared to a reference sequence, has at least 50% homology, more preferably at least 60% homology, more preferably at least 70% homology, more preferably at least 80%, 85%, 90%, 95%, 98% or greater homology to the reference sequence.

To determine the percent homology of two amino acid sequences or of two nucleic acid sequences, the sequences are aligned for optimal comparison purposes (e.g. gaps can be introduced in the sequence of a first amino acid or nucleic acid sequence for optimal alignment with a second amino acid or nucleic acid sequence and the intervening non-homologous sequence in the gap can be disregarded for comparison purposes). There is no requirement for the two sequences to be the same length. Unless otherwise specified, the length of sequence across which the sequences are compared is the entire extent of the alignment. Optionally, the length of a reference sequence aligned for comparison purpose is at least 30%, preferably at least 40%, more preferably at least 50%, even more preferably at least 60%, and even more preferably at least, 70%, 80%, or 90% of the length of the reference sequence.

When a position in the first (reference) sequence is occupied by the same amino acid residue or nucleotide as the corresponding position in the sequence, the molecules are homologous at that position (i.e. there is identity at that position). In the case of nucleic acid sequence comparison there is also homology at a certain position where the codon triplet including the nucleotide encodes the same amino acid in both molecules being compared, due to degeneracy of the genetic code.

The percent homology between two sequences is a function of the number of homologous positions shared by the sequences (i.e., % homology=no. of homologous positions/total no. of positions). Optionally, the comparison of sequences and determination of percent homology can be accomplished using a mathematical algorithm. Suitable algorithms are incorporated in to the NBLAST and XBLAST programs of Altschul et al. (1990) J. Mol. Biol. 215:430-10.

Also comprised within the nucleic acid sequences of the invention are sequences which hybridize to the reference SEQ ID NO:1 under stringent conditions. "Stringent" hybridization conditions in the sense of the present invention are defined as those described by Sambrook et al., Molecular Cloning, A Laboratory Manual, Cold Spring Harbor Laboratory Press (1989), 1.101-1.104, i.e. a positive hybridization signal is still observed after washing for 1 hour with 1×SSC buffer and 0.1% SDS at 55° C., preferably at 62° C. and most preferably at 68° C., in particular for 1 hour in 0.2×SSC buffer and 0.1% SDS at 55° C., preferably at 62° C. and most preferably at 68° C.

The sequences of the invention include fragments of the reference nucleic acid sequence. A "fragment" of the 55 kDa protein nucleic acid reference sequence is any part of that sequence comprising at least 10, preferably at least 20, more preferably at least 30, more preferably at least 50, optionally at least 75, or at least 100 consecutive nucleotides. One application of fragments of SEQ ID NO:1 is in the diagnosis of pasteurellosis or infection by virulent *Photobacterium damselae* subsp. *piscicida*. For instance, such fragments may be used as DNA primers in a diagnostic PCR kit.

Another aspect of the invention pertains to vectors, preferably expression vectors, comprising a nucleic acid sequencing encoding p55 (or a portion thereof). As used herein, the term "vector" refers to a nucleic acid molecule capable of transporting another nucleic acid to which it has been linked. One type of vector is a plasmid, which refers to a circular double stranded DNA loop into which additional DNA segments can be ligated. Another type of vector is a viral vector, wherein additional DNA segments can be ligated into the viral genome. Certain vectors are capable of directing the expression of genes to which they are operatively linked. Such vectors are referred to herein as "expression vectors". In general, expression vectors of utility in recombinant DNA techniques are in the form of plasmids. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, operatively linked to the nucleic acid sequence to be expressed. Expression vectors of the invention may be eukaryotic expression vectors used for expression within the intended recipient of the 55 kDa antigen (as a DNA vaccine) or prokaryotic or eukaryotic expression vectors for expression within a host organism other than the final recipient (for production of recombinant antigen vaccines). Alternatively, the recombinant expression vector can be transcribed and translated in vitro, for example using T7 promoter regulatory sequences and T7 polymerase.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g. 55 kDa proteins, deriative forms of p55, fusion proteins of p55 with a heterologous peptide, etc.).

Another aspect of the invention pertains to host cells into which a recombinant expression vector of the invention has been introduced by transformation. A host cell can be any prokaryotic or eukaryotic cell (including a eukaryotic cell within a multicellular eukaryotic organism), such as *E. coli*, insect cells (using baculovirus expression vectors), yeast cells or mammalian cells. Other suitable host cells are known to those skilled in the art (e.g. Goeddel, supra).

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRITS (Pharmacia, Piscataway, N.J.) which fuse glutathione S-transferase (GST), maltose E binding protein, or protein A, respectively, to the target recombinant protein.

Purified native p55 is also encompassed within the scope of the invention, and it can be extracted or purified from *Ph. damselae* cell cultures using conventional protein purification procedures.

The p55 gene can be incorporated into a Nucleic Acid Vaccine (NAV), whereby the NAV is taken up by host cells of a living animal, and expression of the p55 gene takes place within the cytosol. A p55 gene inserted into a DNA vector can be inoculated directly into a fish (e.g. intramuscularly) for expression in vivo within fish cells. Thus, in one aspect of the invention there is provided a nucleic acid vaccine comprising a pharmaceutically acceptable carrier and a DNA plasmid in which a nucleic acid sequence encoding p55 is operably linked to a transcriptional regulatory sequence. Transcriptional regulatory sequences include promoters, polyadenylation sequences and other nucleotide sequences such as the immune-stimulating oligonucleotides having unmethylated CpG dinucleotides, or nucleotide sequences that code for other antigenic proteins or adjuvanting cytokines. The presence of eukaryotic or viral transcriptional regulatory sequence(s) allows expression of the p55 gene in fish cells. The DNA plasmid itself can be replicated in bacterial cells in order to prepare a vaccine composition, but generally lacks transcriptional regulatory sequences permitting p55 gene expression within prokaryotic cells. For optimal in vivo expression it may be preferred to select transcriptional regulatory sequences endogenous to the fish to be vaccinated. For instance, endogenous cytokine or actin gene promoters may be considered. The DNA can be present in naked form or it can be administered together with an agent facilitating cellular uptake (e.g. liposomes or cationic lipids). The technology of DNA vaccination of fish is explained in more detail in U.S. Pat. No. 5,780,448, which is incorporated herein by reference.

The vaccine of the invention is intended for administration to any fish at risk from, or suffering from, pasteurellosis. Examples of susceptible species include: yellowtail (*Seriola quinqueradiata*), ayu (*Plecoglossus altivelis*), red seabream (*Acanthopagrus schlegeli*), black sea bream (*Pagrus major*), snake-head fish (*Channa maculata*), red grouper (*Epinephelus akaara*), oval file fish (*Navodan modestus*), striped bass (*Morone saxatilis*), hybrid striped bass (*M. saxatilis*×*M. Chrysops*)), gilthead seabream (*Sparus aurata*), sea bass (*Dicentrarchus labrax*), mullet (*Mugil* sp.), yatable blenny (*Pictiblennius yatabei*), Japanese flounder (*Paralichthys olivaceus*) and sole (*Solea senegalensis*).

The typical routes of administration of the vaccine are by injection into the muscle (in particular, apical muscle) or peritoneal cavity (for larger fish), orally in feed, or by immersion in sea water or in fresh water. A preferred vaccination route of an antigenic vaccine is by intraperitoneal injection. It is recommended that fish be at least 2 grams, preferably 10 grams or greater in body weight for administration of the vaccine of the invention by injection. Because certain species of fish are most vulnerable to pasteurellosis when young (such as gilthead sea bream and sea bass), it may be preferred to vaccinate the fish at a weight of 50 g or less, optionally by immersion. For immersion or oral administration, a body weight of at least 2 grams is preferred.

The vaccine of the invention may be administered to fish for prophylactic or therapeutic purposes.

The effective dosage of vaccine may vary depending on the size and species of the subject, and according to the mode of administration. The optimal dosage can be determined through trial and error by a veterinarian or aquaculture specialist. Due to the stress suffered by fish in response to vaccination, it is preferred that the vaccine is provided as a single shot vaccine, in single dosage form. Vaccines may suitably comprise between about 1 μg and 1000 μg, preferably between about 10 μg and 200 μg, more preferably between about 50 μg and 100 μg of recombinant or purified protein in a single dosage. Preferably a single dosage unit is administered to the fish to be treated. For injectable vaccines, a single dosage unit is suitably 0.025 to 0.5 ml, preferably 0.05 to 0.2 ml, optionally about 0.1 ml, in volume.

For DNA vaccines, a minimum dosage of 10 pg up to dosages of 1000 μg of plasmid per animal should be sufficient for suitable expression of the antigen in vivo.

Typically, vaccines are prepared as liquid solutions, suspensions, or emulsions for injection or for delivery through the ambient water. For instance, a liquid emulsion or emulsifiable concentrate can be prepared in order to be added to a water tank, bath, or sea cage where the fish are held. Solid (e.g. powder) forms suitable for dissolution in, or suspension in, liquid vehicles, or for mixing with solid food, prior to administration may also be prepared. The vaccine may be lyophilized, optionally freeze-dried, in a ready to use form for reconstitution with a sterile diluent or solvent. For instance, lyophilized vaccine may be reconstituted in saline (optionally provided as part of the packaged vaccine product). Nucleic acid vaccines are particularly suited to lyophilisation due to the stability and long shelf-life of the molecules. The pharmaceutical vaccine compositions of the invention may be administered in a form for immediate release or extended release.

In one embodiment of the invention, p55 or a DNA expression vector carrying the p55 coding sequence is combined with a pharmaceutically acceptable carrier or vehicle in a pharmaceutical composition. Pharmaceutically acceptable carriers or vehicles include conventional excipients, and may be, for example, solvents such as water, oil, or saline, dextrose, glycerol, sucrose, tricaine, wetting or emulsifying agents, bulking agents, coatings, binders, fillers, disintegrants, diluents, lubricants, pH buffering agents, or conventional adjuvants such as muramyl dipeptides, pyridine, aluminium hydroxide, oils (e.g. mineral oil), saponins, block co-polymers and other substances known in the art. In a preferred embodiment of the invention, a vaccine composition comprises isolated or purified p55 or a derivative thereof, and an adjuvant. The preferred adjuvant is Freund's incomplete adjuvant. Optionally the p55 protein or derivative is suspended in a saline solution (such as PBS) and emulsified with Freund's incomplete adjuvant in a ratio of about 1:1 by volume.

To immunize a fish, a p55 antigen or p55 gene vector can be administered parenterally, usually by intramuscular injection in an appropriate vehicle, injection into the peritoneal cavity, orally in feed, or by immersion. The preferred antigenic vaccine compositions of the invention are in a form suitable for administration by injection or immersion. DNA vaccination is generally by intra-muscular injection.

In some instances it may be desirable to combine the vaccine of the invention with another antigen or antigens in a combination vaccine, or in a kit comprising one or more components for separate, sequential or simultaneous administration, for treatment or prevention of infections with *Photobacterium damselae* subspecies *piscicida* (formerly *Pasteurella piscicida*) or a multitude of diseases to which the fish are susceptible.

Other antigens with which the vaccine of the invention may be combined include, for example, antigens derived from the following pathogens: *Photobacterium damselae* subspecies *piscicida.*, *Iridovirus* spp., *Nodavirus* spp., *Vibrio* spp., *Edwardsiella* spp., *Streptococcus* spp. *Lactococcus* spp and *Nocardia* spp.

The novel antigens disclosed as part of the present invention are also useful in screening for antibodies to *Ph. damselae*, for instance in the preparation of a diagnostic kit for testing fish for exposure to this bacterium.

Antibodies raised against the purified p55 antigen are also comprised within the invention. It is contemplated that such antibodies could have both diagnostic and therapeutic applications in disease management and fish health. Both polyclonal antibodies and monoclonal antibodies may be useful in this respect. Procedures for immunizing animals, e.g. mice, with proteins and selection of hybridomas producing immunogen-specific monoclonal antibodies are well know in the art (see for example Kohler and Milstein (1975) Nature 256: 495-497). Sandwich assays and ELISA may be mentioned as specific examples of diagnostic assays.

EXAMPLES

Example 1

Cloning and Sequencing of P55 from *Ph. Damselae* Subsp. *Piscicida*

*Ph. damselae* bacteria (strain MT1415) are grown in tryptic soy broth (TSB) supplemented with NaCl to a final concentration of 1% (w/v) (TSB-1) at 22° C. with shaking (100 rpm) to an optical density at 600 nm of approximately 0.6 (mid-exponential phase). Bacterial cells are removed by centrifugation and subsequent filtration through a 0.22 μm pore size filter. Cell-free supernatants are concentrated 100-fold using a Vivaflow 200 concentrator (Sartorius AG, Goettingen), and dialysed against 20 mM Tris-HCl (pH 8.0).

Concentrated culture supernatants are subjected to SDS-PAGE. The 55 kDa band is excised from the gel after Coomassie-blue staining. In situ tryptic digestion of the purified protein and Edman degradation of two HPLC-purified peptides is performed.

The fragments yield the following sequences: NNDKPDASDDKYADYVVR (SEQ ID NO:3) and YTAAATEYTVIDALFHSPTFR (SEQ ID NO:4). The underlined regions are used to design degenerate primers A1 and B, respectively. Total bacterial DNA is prepared from strain MT1415 according to conventional techniques and is used as template for PCR amplifications using primer A1 and B. The 200 bp amplified fragment is excised from an agarose gel, purified using the QIAquick Gel Extraction kit (Qiagen), cloned into the pGEM-T Easy Vector (Promega) following the manufacturer's instructions and sequenced to confirm it corresponds to the desired fragment.

The PCR-derived 200 bp fragment described above is labeled with AlkPhos Direct (Amersham Biosciences) and used as a probe for Southern blot analysis of restriction-enzyme digested total DNA from strain MT1415. DNA from agarose slices containing the relevant reactive fragments is extracted using the QIAquick Gel extraction kit (Qiagen). A 3100 bp HindIII-HindIII fragment is inserted into pBluescript II KS (Stratagene); a 4100 bp NcoI-BamHI fragment is cloned in pET-32b (Novagen). Transformants are selected by PCR using primers A1 and B, and sequenced.

Another DNA probe is generated by PCR using the recombinant plasmid containing the 4000 bp NcoI-BamHI fragment and primers P4 (5'-GGCCATGATGAATCTGAAGG-3') (SEQ ID NO:5) and T7 (5'-GTAATACGACTCACTATAGGGC-3') (SEQ ID NO:6). This DNA fragment is used as a probe on Southern blotting analysis of MT1415 total DNA, following the procedures described above. The region of an agarose gel containing a 1000 bp HindIII-HindIII reactive fragment is excised, the DNA is extracted using the QIAquick Gel Extraction Kit (Qiagen) and cloned into the pBluescript II KS vector (Stratagene). Transformants with the desired construct are identified by PCR using the primers P4 and T7 and sequenced.

The complete DNA sequence of p55 is shown in FIG. 1 (SEQ ID NO:1), and the deduced primary structure is shown in FIG. 2 (SEQ ID NO:2). The protein is 513 amino acids long, and displays a hydropathic profile typical of a non-membrane protein. Analysis of the amino acid sequence using SignalP, version 1.1 (www.cbs.dtu.dk/services/signalP) reveals the existence of a putative signal peptide with a cleavage site between amino acid residues 16 and 17. Fortuitously, one of the sequences obtained by Edman degradation of tryptic peptides from p55 starts at amino acid residue 17, an asparagine. Considering that trypsin does not cleave peptide bonds on the carboxyl side of alanine (residue 16), it can be concluded that asparagine 17 represents the N-terminus of the mature protein. The predicted molecular mass of the mature form of the protein (56.185 kDa) is in agreement with the size estimated by SDS-PAGE. Database searches using the primary structure of p55 reveal some homology between the first 340 amino acid residues of p55 and a putative prophagic protein of unknown function from *E. coli* O157:H7.

Example 2

Expression of p55 in *E. Coli*

PCR fragments containing the full length p55 gene are cloned into two different expression vectors: pET-28a(+) (Novagen) and pQE-31 (Qiagen), yielding the recombinant plasmids pETp55 and pQEp55, respectively. *E. coli* cells are transformed by conventional methods and transformants are grown at 37° C. with shaking for 8 hours in Luria Broth (LB) supplemented with 50 μg/ml kanamycin or with 50 μg/ml kanamycin plus 200 μg/ml ampicillin for the BL21 *E. coli* strain (pET-28 (+) vectors) and M15 *E. coli* strain (pQE-31 vectors), respectively. These cultures are diluted 1:100 in fresh LB with the respective antibiotics and grown for 3 hours at 37° C. with shaking. IPTG is then added to a final concentration of 1 mM and growth continues for 5 hours at 37° C. IPTG-induced cells are pelleted by centrifugation. SDS- PAGE analysis of *E. coli* cells carrying the pETp55 plasmid reveals a robust expression of a non-soluble (present in the inclusion bodies fraction) 57 kDa protein. Western blotting analysis of these cells using the antibody directed to p55 (described in Example 3) confirms the identity of this protein. The apparent molecular mass of this protein is 2 kDa higher than the one displayed by authentic p55, indicating that the signal sequence of the precursor form of p55 is not cleaved in these *E. coli* cells. The insoluble 57 kDa protein does not possess apoptogenic activity.

Western blotting analysis of *E. coli* M15 cells harbouring the pQEp55 expression vector using the antibody against p55 (described in Example 3) reveals a low level of p55 expression. Nevertheless, p55 produced by these recombinant cells displays the correct molecular weight by SDS-PAGE. Furthermore, the expressed protein is found in the soluble fraction obtained after centrifugation of sonicated cells, suggesting that p55 produced in these cells is correctly folded. When these soluble extracts are injected into sea bass, high numbers of apoptotic cells can be observed in the peritoneal cavities 6 hours after injection. The apoptotic effects of the recombinant protein are morphologically indistinguishable from those seen upon injection with purified native p55. Purified native p55 is prepared by diluting concentrated culture supernatants of *Ph. damselae* 1:1 in 2× native-PAGE buffer (the same composition as SDS-PAGE sample buffer, except that no SDS is included and the concentration of beta-mercaptoethanol is reduced to 5 mM) and subsequent separation by 10% Native-PAGE. The lanes on the extremities of the gel are cut, stained with Coomassie blue and used to locate the position of the main protein bands. The slice containing the p55 protein is cut out and minced for extraction by diffusion (at 4° C. with gentle agitation) using 20 mM Tris-HCl (pH 8.0) as elution buffer,

Example 3

Passive Immunization Using Rabbit Antiserum to *Photobacterium* 55 kDa Protein (Three Independent Experiments are Carried Out)

Fish: European sea bass (*Dicentrarchus labrax*) having a body weight of about 100 g are held in glass aquaria with UV sterilized sea water supplied through a biofilter in a recirculating system. The water temperature is a constant 23±1° C. and salinity is 35‰.

Production of immune serum: Hyperimmune serum against the 55 kDa protein is raised in rabbits using 3 doses of the purified protein emulsified in Freund's incomplete adjuvant. The purified p55 protein is prepared as follow. Concentrated culture supernatants from strain MT1415 prepared as described in Example 1 above are subjected to Coomassie-blue SDS-PAGE. After electrophoretic separation, the 55 kDa band is excised from the gel, minced in elution buffer (0.02% SDS, 10 mM beta-mercaptoethanol, 34 mg/ml PMSF) and incubated overnight at 4° C. with shaking. The acrylamide suspension is then centrifuged at 3000 g for 15 min at 4° C. The supernatant is collected and centrifuged again in the same conditions. The supernatant is collected, frozen at −80° C. and lyophilized. Then the lyophilized protein is resuspended in 2 ml distilled water and the protein is precipitated with acetone (90% v/v) overnight at −20° C. The precipitated protein is recovered by centrifugation at 3000 g for 10 min at 4° C., washed with 90% (v/v) acetone, dried overnight at room temperature and resuspended in PBS. Rabbits are bled 1 week following the final immunization. Control serum is pre-immune serum from the same rabbit.

Challenge: The *Ph. damselae* subsp. *piscicida* strain PTAVSA95 is thawed and inoculated in tryptone soy agar containing 1% NaCl (TSA-1). Cultures are grown overnight and then resuspended in tryptone soy broth agar containing 1% NaCl (TSB-1). The bacterial density is measured by spectrophotometry (Beckman DU-65) at 600 nm and dilutions are made until the expected number of colony forming units (CFU) predicted by a curve absorbance/CFU determined previously. Real CFU used as a challenge dose are checked by viable counts of dilutions in TSB-1 spread on TSA-1 plates 48 h after inoculation at 24° C. The challenge inoculum is drawn into syringes and each fish inoculated by intraperitoneal (i.p.) injection with 100 µl. For the confirmation of the cause of death the pathogen is re-isolated from the head kidney and/or dead fish by culturing onto TSA-1.

Before vaccination and challenge all fish are anaesthetized in 0.003% (v/v) ethylene glycol monophenyl ether.

Experiment 1

One group of 8 fish receives 100 µl per fish of 1$^{st}$ bleed rabbit antiserum raised against the 55 kDa protein, by intraperitoneal injection. One group of 8 fish receives 300 µl per fish 1$^{st}$ bleed rabbit antiserum in the same manner. A final control group of 8 fish receives 300 µl per fish of normal rabbit serum. No negative control groups are required due to the highly-characteristic mortalities resulting from *Photobacterium* infection. Fish from each test group are held in independent tanks. Immediately following vaccination, while still under anaesthetic, each fish receives a challenge dose of $2.24\times10^7$ *Photobacterium* colony forming units (CFUs).

Experiment 2

One group of 8 fish receives 300 µl per fish of 1$^{st}$ bleed rabbit antiserum raised against the 55 kDa protein, by i.p. injection. One group of 8 fish receives 300 µl per fish of 2$^{nd}$ bleed rabbit antiserum. A control group of 8 fish receives 300 µl per fish of normal rabbit serum. Fish from each test group are held in independent tanks. Immediately following vaccination, while still under anaesthetic, each fish receives a challenge dose of $1.87\times10^7$ *Photobacterium* colony forming units (CFUs).

Experiment 3

One group of 8 fish receives 300 µl per fish of 2$^{nd}$ bleed rabbit antiserum raised against the 55 kDa protein, by i.p. injection. A control group of 8 fish receives 300 µl per fish of normal rabbit serum. Fish from each test group are held in independent tanks. Immediately following vaccination, while still under anaesthetic, each fish receives a challenge dose of $2.24\times10^7$ *Photobacterium* colony forming units (CFUs).

The first mortalities occur on day 1 post challenge, whilst the final mortality occurs on day 5. No further mortalities occur for 8 consecutive days, so the trial is terminated 15 days after immunization and challenge.

Results

While this is only a small scale study, the indications are that antibodies against the 55 kDa protein from *Ph. damselae* ECP are effective in protection against an experimental challenge (Table 1). The protective effect is pronounced, particularly when it is considered that rabbit immunoglobulins are unable to activate the teleost complement cascade. Furthermore, the fish will mount an immune response against the rabbit immunoglobulins, reducing antibody numbers and consequently reducing their efficacy further. Thus, the level of protection indicated in this study is highly significant and makes the 55 kDa protein a key potential target for development of vaccines against this economically important disease.

TABLE 1

| Experiment | Vaccine | cumulative mortality (%) | RPS | RPS calculated relative to: |
|---|---|---|---|---|
| 1 | Immune serum 100 μl/1st bleed | 63 | 17 | control rabbit normal serum |
| 1 | Immune serum 300 μl/1st bleed | 38 | 50 | control rabbit normal serum |
| 1 | Normal serum 300 μl | 75 | — | n/a |
| 2 | Immune serum 300 μl/1st bleed | 25 | 50 | control rabbit normal serum |
| 2 | Immune serum 300 μl/2nd bleed | 0 | 100 | control rabbit normal serum |
| 2 | Normal serum 300 μl | 50 | — | n/a |
| 3 | Immune serum 300 μl/2nd bleed | 13 | 67 | control rabbit normal serum |
| 3 | Normal serum 300 μl | 38 | — | n/a |

Example 4

Vaccination with p55 as Inclusion Bodies and in Formalin Inactivated ECPs

Fish: European sea bass (*Dicentrarchus labrax*) juveniles having a body weight of about 25 g at time of vaccination are held at 26±1° C. with UV and, when necessary, ozone-sterilised saltwater (30‰) supplied through a biofilter in a recirculating system.

Vaccines: p55 inclusion bodies—BL21 *E. coli* strain transformed with the pETp55 plasmid (see Example 2) are grown overnight with agitation (120 rpm) in Luria Broth (LB) supplemented with 50 μg/ml kanamycin. The culture is then used to inoculate (1:100) fresh LB supplemented with 50 μg/ml kanamycin and grown for 2 hours at 37° C. with shaking. Cells are induced by adding IPTG to a final concentration of 0.1 mM and growth continued for 3 hours as above. IPTG-induced cells are pelleted by centrifugation (15 min, 5000 rpm), resuspended in 10 ml Buffer A (10 mM $NaPO_4$ pH 7.2, 0.2M NaCl, 1 mM EDTA, 1:1000 PMSF at 50 mg/ml, 1:10000 beta-mercaptoethanol) and sonicated 3 times for 25 seconds (1 minute interval) in ice. After transferring to Eppendorf tubes (1 ml/tube) and centrifuging (15 min, 13000 g) the supernatant is discarded and 1 ml buffer A added to each tube. The pellet is then resuspended by sonicating in ice 4 times for 10 seconds (1 min interval) and after centrifugation (15 min, 13000 g) the supernatant is discarded. The pellet is resuspended by adding 1 ml buffer B (=Buffer A+1% Triton X-100) and sonicating in ice 4 times for 10 seconds (1 minute interval). After centrifuging as above and discarding the supernatant, the pellet is resuspended in 1 ml Buffer A by sonicating in ice 4 times 10 seconds (1 minute interval). The inclusion bodies are collected by centrifugation, resuspended as above in PBS (p55 final concentration 1 mg/ml) and emulsified 1:1 in Freund's incomplete adjuvant.

p55 enriched ECPs—55 kDa protein enriched (>85%) extracellular products (ECPs) from *Ph. damselae* subsp. *piscicida* at mid exponential growth phase are prepared as described in Example 1. Before the immunization, the ECPs are diluted to 2 μg of protein/μl and inactivated by adding 0.5% (v/v) of formaldehyde (37% formalin solution, Sigma) for 24 hours at 4° C. Any remaining formalin is neutralized by adding 0.04% (v/v) of a 2M sodium thiosulphate solution. 55 kDa enriched ECPs are then emulsified 1:1 in Freund's incomplete adjuvant.

Vaccination: One group of 54 fish receives 50 μl of the inclusion bodies vaccine per fish by i.p. injection. One group of 43 fish receives 50 μl of 55 kDa enriched ECPs vaccine per fish in the same manner. One control group of 42 fish (adjuvant control) receives 50 μl of PBS emulsified 1:1 in Freund's incomplete adjuvant per fish by i.p. injection, and another group of 26 fish (uninjected control) is left untreated. Fish from each test group are held in independent tanks.

Challenge: the same strain and procedure described in Example 3 are used to prepare the challenge inoculum except that the challenge dose is $5.2 \times 10^6$ CFUs in 50 μl per fish. Challenge was performed 650° D after vaccination. For confirmation of death the pathogen is re-isolated from the head kidney of moribund and/or dead fish by culturing onto TSA-1.

The first mortalities occur on day 2 post-challenge, whilst the final mortality occurs on day 8. No further mortalities occur for 8 consecutive days, so the trial is terminated 15 days after challenge.

Results

The results (shown in Table 2) clearly indicate that both the p55 inclusion body vaccine and the inactivated p55 enriched ECP vaccine are effective in protecting fish against experimental infections with *Ph. damselae*. The fact that similar levels of protection were achieved suggests that p55, and not any other contaminant *Ph. damselae* or *E. coli* protein, is the protective antigen.

TABLE 2

| Vaccine | Cumulative mortality (%) | RPS (relative to adjuvant control) | RPS (relative to uninjected control) |
|---|---|---|---|
| p55 inclusion bodies | 24 | 61 | 63 |
| p55 enriched ECPs | 19 | 70 | 72 |
| Adjuvant control | 62 | n/a | 5 |
| Uninjected control | 65 | −6 | n/a |

Example 5

Vaccination with p55 as Inclusion Bodies to Demonstrate Protection Against Japanese *Ph. damselae* Strains.

Fish: European sea bass (*Dicentrarchus labrax*) juveniles having a body weight of about 7-10 g at time of vaccination are held at 22±1° C. with UV and, when necessary, ozone-sterilised saltwater (30‰) supplied through a biofilter in a recirculating system.

Vaccines: p55 inclusion bodies—BL21 *E. coli* strain transformed with the pETp55 plasmid (see Example 2) are grown overnight with agitation (120 rpm) in Luria Broth (LB) supplemented with 50 μg/ml kanamycin. The culture is then used to inoculate (1:100) fresh LB supplemented with 50 μg/ml kanamycin and grown for 2 hours at 37° C. with shaking. Cells are induced by adding IPTG to a final concentration of 0.1 mM and growth continued for 3 hours as above. IPTG-induced cells are pelleted by centrifugation (15 min, 5000 rpm, SORVAL rotor GS-3), resuspended in 20 ml Buffer A per liter of culture media (10 mM $NaPO_4$ pH 7.2, 0.2M NaCl, 1 mM EDTA, 1:1000 PMSF at 50 mg/ml, 1:10000 beta-mercaptoethanol), transferred to SORVAL SS-34 tubes (10 ml/tube) and sonicated 3 times for 30 seconds (1 minute interval) in ice. After centrifuging (15 min, 13000 g), the supernatant is discarded and 10 ml buffer A added to each tube. The pellet is then resuspended by sonicating in ice 4 times for 30 seconds (1 min interval) and after centrifugation (15 min, 13000 g) the supernatant is discarded. The pellet is resuspended by adding 10 ml buffer B (=Buffer A+1% Triton X-100) and sonicating in ice 4 times for 30 seconds (1 minute interval). After centrifuging as above and discarding the supernatant, the pellet is resuspended in 1 ml Buffer A by sonicating in ice 3 times 30 seconds (1 minute interval). The inclusion bodies are collected by centrifugation, resuspended as above in PBS and stored at $-20^2$C until use.

The p55 content of the inclusion bodies is determined by densitometry analysis of an SDS-Page gel using Bovine Serum Albumin (BSA) standards. P55 inclusion bodies are diluted to the required concentration in PBS and emulsified 1:1 in Freund's incomplete adjuvant in order to give a final concentration of approximately 25 micrograms of recombinant p55 protein/dose.

Vaccination: There are two treatments, with two replicates (63 plus 65 fish, respectively) for the vaccinated group and a single group (70 fish) used as control. Each vaccinated fish receives 100 μl of the inclusion bodies vaccine by i.p. injection. Each control fish receives 100 μl of PBS emulsified 1:1 in Freund's incomplete adjuvant per fish by i.p. injection. Fish from each test group are held in independent tanks.

Challenge: The challenge inoculum is prepared as described in Example 3 but the Ph. damselae used is the Japanese strain PP3, and the challenge dose is $5.0\times10^3$ CFUs in 100 μl per fish. For confirmation of death the pathogen is re-isolated from the head kidney of moribund and/or dead fish by culturing onto TSA-1.

The first mortalities occur on day 3 post-challenge, whilst the final mortality occurs on day 7 (vaccinated group) and day 11 (control group). No further mortalities occur for 19 consecutive days, so the trial is terminated 30 days after challenge.

Results

The results (shown in Table 2) clearly indicate that the p55 inclusion body vaccine is effective in protecting fish against experimental infections with the Japanese strain PP3 of *Ph. damselae*.

TABLE 3

| Vaccine | Cumulative mortality (%) | RPS calculated relative to Adjuvant control |
|---|---|---|
| p55 inclusion bodies | 18 | 62 |
| Adjuvant control (PBS/FIA) | 49 | N/A |

The invention claimed is:

1. A method of preparing a vaccine against pasteurellosis, comprising:

(a) growing *Photobacterium damselae* subsp. *piscicida* cells to mid-exponential phase in culture;

(b) separating supernatant from the cells, where a 55 kDa apoptogenic protein is the major protein present in the supernatant; and (c) inactivating the supernatant with an inactivating agent.

2. The method of claim 1, where the culture contains iron at a concentration of less than 15 μM.

3. The method of claim 1, where the culture contains iron at a concentration of less than 10 μM.

4. The method of claim 1, where the culture contains iron at a concentration of less than 1 μM.

5. The method of claim 1, where the culture contains iron at a concentration of less than 0.1 μM.

6. The method of claim 1, comprising concentrating the supernatant prior to inactivating the supernatant.

7. The method of claim 1, comprising incorporating the supernatant that has been inactivated into a vaccine.

8. A method of preparing a vaccine against pasteurellosis, comprising:

(a) growing *Photobacterium damselae* subsp. *piscicida* cells to mid-exponential phase in culture;

(b) separating supernatant from the cells, where a 55 kDa apoptogenic protein is the major protein present in the supernatant;

(c) concentrating the supernatant;

(d) inactivating the supernatant; and (e) incorporating the supernatant into a vaccine.

9. The method of claim 8, where the culture contains iron at a concentration of less than 15 μM.

10. The method of claim 8, where the culture contains iron at a concentration of less than 10 μM.

11. The method of claim 8, where the culture contains iron at a concentration of less than 1 μM.

12. The method of claim 8, where the culture contains iron at a concentration of less than 0.1 μM.

13. A method of preparing a vaccine against pasteurellosis, comprising:

(a) growing *Photobacterium damselae* subsp. *piscicida* cells to mid-exponential phase in a culture that is not supplemented with iron;

(b) separating supernatant from the cells;

(c) purifying a 55 KDa apoptogenic protein from the supernatant;

(d) inactivating the protein; and (e) incorporating the protein into a vaccine.

14. The method of claim 13, where the 55 kDa apoptogenic protein is the major protein present in the supernatant.

15. The method of claim 13, where the culture contains iron at a concentration of less than 15 μM.

16. The method of claim 13, where the culture contains iron at a concentration of less than 10 μM.

17. The method of claim 13, where the culture contains iron at a concentration of less than 1 μM.

18. The method of claim 13, where the culture contains iron at a concentration of less than 0.1 μM.

* * * * *